US011883236B2

(12) United States Patent
Liu et al.

(10) Patent No.: US 11,883,236 B2
(45) Date of Patent: Jan. 30, 2024

(54) METHODS AND SYSTEMS FOR DETECTING SUB-TISSUE ANOMALIES

(71) Applicant: The Board of Regents of the University of Texas System, Austin, TX (US)

(72) Inventors: Hanli Liu, Arlington, TX (US); Venkaiah C. Kavuri, Lake Forest, CA (US)

(73) Assignee: The Board of Regents of the University of Texas System, Austin, TX (US)

( * ) Notice: Subject to any disclaimer, the term of this patent is extended or adjusted under 35 U.S.C. 154(b) by 824 days.

(21) Appl. No.: 15/307,504

(22) PCT Filed: Apr. 29, 2015

(86) PCT No.: PCT/US2015/028342
§ 371 (c)(1),
(2) Date: Oct. 28, 2016

(87) PCT Pub. No.: WO2015/168319
PCT Pub. Date: Nov. 5, 2015

(65) Prior Publication Data
US 2017/0049417 A1 Feb. 23, 2017

Related U.S. Application Data

(60) Provisional application No. 61/985,905, filed on Apr. 29, 2014.

(51) Int. Cl.
*A61B 8/00* (2006.01)
*A61B 8/08* (2006.01)
(Continued)

(52) U.S. Cl.
CPC .......... *A61B 8/4483* (2013.01); *A61B 5/0035* (2013.01); *A61B 5/0073* (2013.01);
(Continued)

(58) Field of Classification Search
CPC . A61B 8/4483; A61B 8/14552; A61B 8/4254; A61B 5/6847; A61B 1/00137;
(Continued)

(56) References Cited

U.S. PATENT DOCUMENTS 4,726,651 A * 2/1988 Wei .................... G02B 6/02033
385/12
5,259,837 A * 11/1993 Van Wormer ........ A61B 8/0833
600/435

(Continued)

FOREIGN PATENT DOCUMENTS

JP 2004073559 A * 3/2004
WO WO-2013/084094 A1 6/2013

*Primary Examiner* — Chao Sheng
(74) *Attorney, Agent, or Firm* — Winstead PC

(57) ABSTRACT

A diagnostic imaging device includes a probe that uses both an ultrasound transducer and frequency-domain diffuse optical imaging (FD-DOI) to assist with locating and diagnosing sub-tissue anomalies. According to one aspect, the diagnostic imaging device relates to a clip-on cap that can be utilized with existing ultrasound transducers. The diagnostic imaging device described herein can be utilized for image-guided needle biopsy to regions where prostate tissues are highly suspicious for high-grade cancer, as well as for image guided interventions, such as cryotherapy, photodynamic therapy, and brachytherapy for early-stage or localized prostate cancer.

4 Claims, 7 Drawing Sheets

(51) Int. Cl.
  *A61B 5/00* (2006.01)
  *A61B 5/1455* (2006.01)
  *A61B 8/12* (2006.01)

(52) U.S. Cl.
  CPC ........ *A61B 5/0084* (2013.01); *A61B 5/14552* (2013.01); *A61B 5/4381* (2013.01); *A61B 5/6847* (2013.01); *A61B 8/085* (2013.01); *A61B 8/12* (2013.01); *A61B 8/4254* (2013.01); *A61B 8/445* (2013.01); *A61B 8/4411* (2013.01); *A61B 8/4416* (2013.01); *A61B 8/5207* (2013.01); *A61B 5/4887* (2013.01); *A61B 2576/02* (2013.01)

(58) Field of Classification Search
  CPC . A61B 8/14522; A61B 8/4411; A61B 8/4416; A61B 8/085; A61B 8/5207; A61B 8/44; A61B 5/0059; A61B 8/00; A61B 8/12; A61B 8/445; A61B 5/0035; A61B 5/0073; A61B 5/0084; A61B 5/14552; A61B 5/4381; A61B 5/4887; A61B 2576/02
  See application file for complete search history.

(56) References Cited

U.S. PATENT DOCUMENTS

| | | | |
|---|---|---|---|
| 2006/0167473 A1* | 7/2006 | Scheyer | A61B 1/00177 606/139 |
| 2006/0253007 A1* | 11/2006 | Cheng | A61B 5/0048 600/310 |
| 2010/0056916 A1 | 3/2010 | Bakker et al. | |
| 2010/0256461 A1* | 10/2010 | Mohamedali | A61B 5/0086 600/301 |
| 2011/0268362 A1* | 11/2011 | Toma | A61B 5/0091 250/349 |
| 2012/0320385 A1* | 12/2012 | Mu | G01B 11/22 356/624 |
| 2014/0180116 A1* | 6/2014 | Lindekugel | A61B 8/4455 600/461 |
| 2015/0305712 A1* | 10/2015 | Urano | A61B 5/0075 600/440 |
| 2015/0346900 A1* | 12/2015 | Wang | G06F 1/16 345/174 |

\* cited by examiner

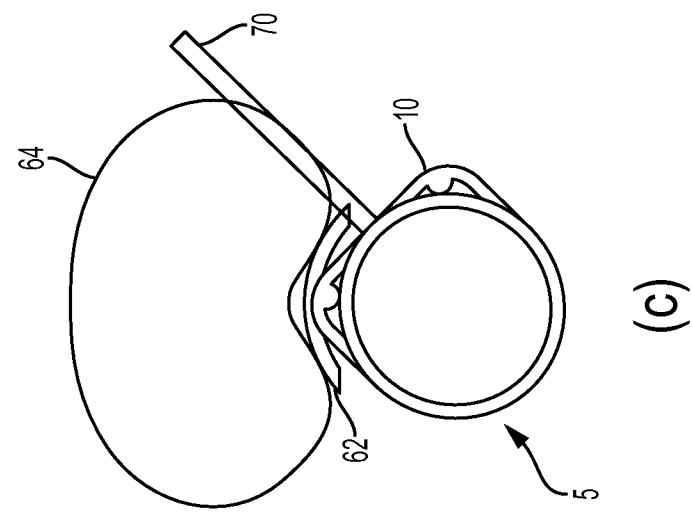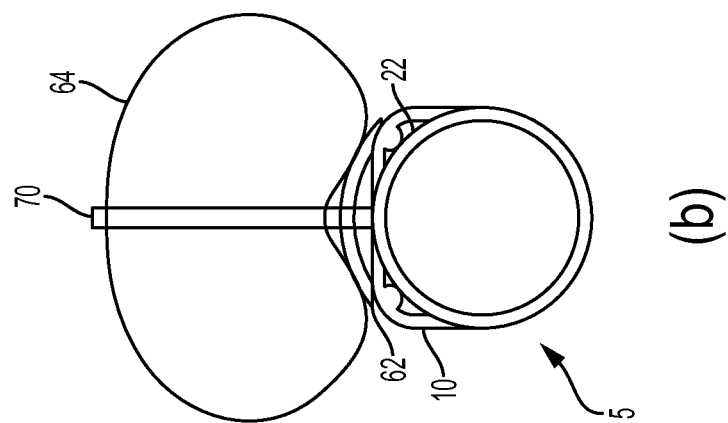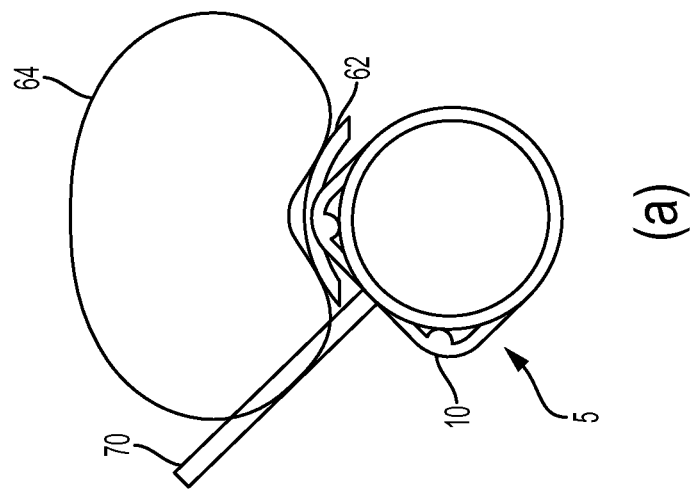
FIG. 7

METHODS AND SYSTEMS FOR DETECTING SUB-TISSUE ANOMALIES

CROSS-REFERENCE TO RELATED APPLICATIONS

This application claims the benefit of U.S. Provisional Patent Application Ser. No. 61/985,905, filed on Apr. 29, 2014, which is incorporated herein by reference in its entirety.

STATEMENT OF FEDERALLY FUNDED RESEARCH

This invention was made with government support under R01CA138662 awarded by the National Institutes of Health (NIH) and W81XWH-09-1-0406 awarded by the Department of Defense (DOD). The government has certain rights in the invention.

FIELD OF THE INVENTION

The present invention relates generally to novel diagnostic imaging devices and systems for screening and diagnosis of prostate cancer. According to one aspect, the present invention relates to a probe that uses both an ultrasound transducer and frequency-domain diffuse optical imaging (FD-DOI) to assist with locating and diagnosing sub-tissue anomalies. According to another aspect, the present invention relates to a clip-on cap that can be easily utilized with existing ultrasound transducers. The diagnostic imaging device described herein can be utilized for image-guided needle biopsy to regions where prostate tissues are highly suspicious for high-grade cancer, as well as for image-guided interventions, such as cryotherapy, photodynamic therapy, and brachytherapy for early-stage or localized prostate cancer. Overall, the diagnostic imaging system can be utilized for (1) early detection of aggressive prostate cancer, (2) cancer staging of suspicious lesions, (3) longitudinal monitoring and active surveillance, (4) reduction of unnecessary biopsy procedures, (5) selection of the most effective and least invasive treatment, and (6) reduction of medical burden on health care systems, and (7) improvement of patients' quality of life. The device provides an indirect measure of cellular morphology of prostate cancer and provides data that will enhances the understanding of longitudinal changes of in vivo cellular morphology of aggressive prostate cancer, which may be ultimately used for active surveillance to avoid overtreatments.

BACKGROUND

One in six men is diagnosed with prostate cancer (PCa). It is predicted that in 2014, more than 233,000 men will be diagnosed with PCa, and almost 30,000 men will die of the disease. Ideally, if diagnoses of both slow-growing low-risk PCa and aggressive high-risk PCa were more accurate, low-grade PCa could be safely watched with active surveillance without overtreatment, while high-grade cancers could be treated on time and effectively. In this way, overtreatments for low-risk, low-grade PCa could be avoided, which would reduce medical, physical, and mental burdens on cancer patients as well as financial burdens on health care systems. Also, accurate detection of low-risk PCa can prevent severe post-treatment side-effects, such as impotence or incontinence or both. However, the current clinical diagnosis for PCa relies on needle biopsy through transrectal-ultrasound (TRUS) guidance. Since the sensitivity and specificity of TRUS for detecting PCa have proven to be ineffective, TRUS has served as a navigation tool only to guide a needle biopsy of the prostate. The current diagnostic needle biopsy is rather "blind." Biopsy samples are collected almost blindly without knowing whether or not the biopsied lesions are highly specious for aggressive cancer. Although many technologies in medical imaging are developed or are being developed to image PCa, including MRI-guided needle biopsy, no accurate, portable imaging tools are available to clinicians, allowing them to differentiate aggressive PCa from indolent PCa. Therefore, more research and technology development are urgently needed to explore a reliable imaging means for improved detection of aggressive PCa.

Near infrared spectroscopy (NIRS) is an optical spectroscopic technology that can quantify concentrations of oxygenated hemoglobin (HbO), deoxygenated/reduced hemoglobin (HbR), and light scattering in living when two or more wavelengths between 670-900 nm are used. As compared to MRI, the NIRS technology is portable, more immune to motion artifacts, less restricted to body confinement in human subjects, and feasible to use for a large population of subjects as well as for doctor-office-based measurements. Moreover, diffuse optical tomography (DOT) is based on diffusion theory and is able to process multi-channel NIRS data to form images. DOT can be categorized into time-domain (TD), frequency-domain (FD), and continuous-wave (CW) format, depending on how light is delivered. Both TD- and FD-DOTs permit quantifications of light absorption ($\mu_a$) and light scattering ($\mu_s'$) based on diffusion theory, while CW systems do not allow the separation these two optical quantities ($\mu_a$, and $\mu_s'$). However, FD-DOT is often used for cancer studies because of its much lower cost and faster data acquisition, as compared to TD-DOT. Therefore, in the past 2 decades, FD-DOT has been investigated with a significant amount of research efforts by various groups to characterize human breast tissues and to detect/diagnose breast cancer. A recent report indicates that DOT holds great promises for detecting disease in mammographically dense tissue, distinguishing between malignant and benign lesions and for understanding the impact of neoadjuvant chemotherapies.

By comparison, investigation of PCa by DOT has been very limited. In reality, it is difficult to collect baseline $\mu_a$ and $\mu_s'$ values of a normal human prostate, partially because of lack of an appropriate imaging tool to reach the human prostate non-intrusively. Recent studies reported that DOT coupled to a TRUS probe, as a minimally intrusive approach, is promising for improved diagnosis of PCa if the location of cancer is known. However, the weakness of this method is the required prior knowledge of PCa locations, which are not available by current TRUS imaging facilities.

Since cancer tissues are more vasculature than the surrounding tissue, hemoglobin-based absorption in tumors provides optical contrast in DOT. When imaged at multiple wavelengths, DOT is capable of measuring chromophore concentrations such as oxy-hemoglobin, deoxy-hemoglobin, and water. Usage of DOT for breast cancer detection and diagnosis has been extensively studied for nearly 20 years. However, investigations on detection of prostate cancer using DOT have been relatively limited compared to those done for breast cancer detection. A previous ex-vivo study reported differences in water content between normal and cancer human prostate tissues. A recent review paper has provided a comprehensive summary of optical properties of human prostate cancer tissue at selective wavelengths. Specifically, several reports given in references show that light scattering of prostate cancer tissue is higher than that of normal prostate tissue. Trans-rectal DOT has been also reported by several recent studies as a possible imaging tool for prostate cancer detection and diagnosis.

DOT instrumentation can be divided into three categories based on the principle of operation: 1) time-resolved systems, 2) frequency-domain systems, and 3) continuous wave (CW) systems. Measurements are made in transmission geometry, reflection geometry, or both. A time-resolved system relies on photon counting or gated imaging, which provides photons' time of flight through the tissue. However, these systems are costly in comparison with CW systems. A frequency-domain system modulates laser light typically in the radio frequency range (100 MHz) and measures the amplitude and phase shift of the detected signal. A CW system is the simplest, fastest, and most cost-effective system in data collection; it can also be made at a video rate for imaging. However, CW systems measure only the intensity of reflected/transmitted light, so they cannot separate the absorption property from the scattering effect of the tissue.

In order for trans-rectal DOT to be able to provide excellent reconstructed images for prostate cancer detection, obstacles must be acknowledged in order to find appropriate solutions. One main obstacle is closely associated with the location of measurements: the human rectum, where space is limited (allowing a limited number of optodes to be implemented). Furthermore, only reflectance geometry of DOT can be utilized. Given the nature of light scattering in tissues, DOT suffers from poor spatial resolution. Measurements taken using reflectance geometry do not normally achieve the excellent spatial resolution that is more commonly obtained in those taken by transmission geometry. One way to improve the spatial resolution is to couple DOT with other imaging techniques such as MRI and ultrasound. In particular, a combined TRUS and DOT probe for imaging prostate cancer has been studied previously, utilizing the anatomical information from ultrasound to reduce the number of unknowns in the DOT image reconstruction. While the combined TRUS-DOT method improves accuracy of reconstructed DOT images, it relies highly on the ability of TRUS to locate the prostate cancer lesion. Given the fact that TRUS has a low prostate cancer detection accuracy and that each region is assumed to be homogenous, the reconstructed DOT images of prostate cancer could be erroneous.

SUMMARY

The present invention provides, among other things: 1) a TRUS-integrated FD-DOI (TRUS/FD-DOI) cap that will house all the needed optic fibers and touch-sensing wires and yet be easily clipped onto existing clinical TRUS probes; and 2) a hybrid reconstruction technique that combines a piecewise cluster reconstruction approach with anatomical information about a prostate that was collected from the TRUS.

The invention utilizes a hierarchical scheme of clustering where a cluster is defined as a group of nodes/voxels within a predefined volume. By utilizing hierarchical clustering, a region of interest (ROI, e.g., the prostate) can be transformed into a partially heterogeneous medium, within which can then be searched and further possible cancer lesions can be reconstructed. The inverse problem of DOT is solved in multiple steps by changing cluster sizes within the image domain. Multi-step reconstruction in DOT has been reported earlier for breast cancer detection based on a frequency-domain study. It is understood that the size and location of the absorber were partially or roughly estimated in the first step of reconstruction, after which more steps were utilized to further improve the quality of reconstructed images. In the TRUS-DOT scenario, however, a rough reconstruction of the first step is futile to effectively detect prostate cancer due to the multi-layer tissue compositions, reflectance measurement geometry, limitation in the number of measurements, and particularly the inability of ultrasound to identify prostate cancer lesion or lesions. Thus, to improve the effectiveness and accuracy of prostate cancer imaging, a piecewise division of the image domain in DOT can be used. It is assumed that the domain consists of disjoint sub domains with different optical properties.

Specifically, the invention presents a piecewise division of the image domain for a human prostate in the inverse calculation. By using DOT, it is possible to combine the piecewise division with hard-prior anatomic information for DOT image reconstruction.

In one aspect, the invention includes an ultrasound transducer cap includes a hollow body with an internal cavity that compliments an ultrasound transducer. The hollow body includes an ultrasound transducer cutout disposed along a length of the hollow body that provides an unblocked line of sight between an ultrasound transducer within the hollow body and rectal wall. The hollow body also may include one or more light emitters disposed along an edge of the ultrasound transducer cutout, and one or more light detectors disposed along an edge of the ultrasound transducer cutout. In some aspects, the hollow body includes a touch sensitive electrode disposed on an outer surface of the hollow body to detect contact with a tissue.

In one aspect, the invention includes a hierarchical clustering method of detecting sub-tissue anomalies. The method includes contacting a rectal wall with a probe, wherein the probe includes an ultrasound transducer for collecting anatomical data about a tissue; a first light emitter disposed in proximity to the ultrasound transducer for emitting light into a first location of the tissue; and a first light detector disposed in proximity to the ultrasound transducer for detecting the emitted light from the first light emitter within the first location of the tissue. The method further includes using the ultrasound transducer to collect ultrasound data about an anatomical structure of the tissue; emitting light from the first light emitter into the tissue; collecting light scatter data about the tissue with the first light detector; reconstructing the ultrasound data and the light scatter data to correlate the anatomical structure of the tissue with the light scatter data; dividing the reconstructed data into geometric clusters; analyzing the geometric clusters to identify suspicious segments having greater light scatter; dividing the suspicious segments having greater light scatter into smaller geometric clusters; and analyzing the smaller geometric clusters to refine a location for areas with greater light scatter.

In one aspect, the invention includes a system for detecting sub-tissue anomalies. The system includes a probe coupled to an oximeter and a processor. The probe includes an ultrasound transducer for collecting anatomical data about a tissue; a first light emitter disposed in proximity to the ultrasound transducer for emitting light into a first location of the tissue; and a first light detector disposed in proximity to the ultrasound transducer for detecting the emitted light from the first light emitter within the first location of the tissue. The oximeter is coupled to the probe and provides light to and receives detected scattered light from the probe. The oximeter includes a first optical fiber that provides light to the first light emitter, and a second optical fiber that receives scattered light from the first light detector. The processor is coupled to the oximeter and reconstructs data received from the ultrasound transducer with data from the oximeter to correlate both data sets.

In other aspects, the system includes a second light emitter coupled to the oximeter and disposed in proximity to the ultrasound transducer for emitting light into a second location of the tissue; a second light detector coupled to the oximeter via a fourth optical fiber and disposed in proximity to the ultrasound transducer for detecting scattered light within the second location of the tissue; a first optical switch disposed between the oximeter and the first and second light emitters to sequentially distribute light to the first and second light emitters; and a second optical switch disposed between the oximeter and the first and second light detectors to sequentially receive the scattered light from the first and second light detectors. The system may also include an ultrasound fiducial disposed in proximity to the first light detector; an accelerometer disposed within a probe body to provide orientation data about the probe.

The terms "a" and "an" are defined as one or more unless this disclosure explicitly requires otherwise. The term "substantially" is defined as largely but not necessarily wholly what is specified (and includes what is specified; e.g., substantially 90 degrees includes 90 degrees and substantially parallel includes parallel), as understood by a person of ordinary skill in the art. In any disclosed embodiment, the terms "substantially," "approximately," and "about" may be substituted with "within [a percentage] of" what is specified, where the percentage includes 0.1, 1, 5, and 10 percent.

Further, a device or system that is configured in a certain way is configured in at least that way, but it can also be configured in other ways than those specifically described.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, an apparatus that "comprises," "has," "includes" or "contains" one or more elements possesses those one or more elements, but is not limited to possessing only those elements. Likewise, a method that "comprises," "has," "includes" or "contains" one or more steps possesses those one or more steps, but is not limited to possessing only those one or more steps.

Any embodiment of any of the apparatuses, systems, and methods can consist of or consist essentially of rather than comprise/include/contain/have any of the described steps, elements, and/or features. Thus, in any of the claims, the term "consisting of" or "consisting essentially of" can be substituted for any of the open-ended linking verbs recited above, in order to change the scope of a given claim from what it would otherwise be using the open-ended linking verb.

The feature or features of one embodiment may be applied to other embodiments, even though not described or illustrated, unless expressly prohibited by this disclosure or the nature of the embodiments.

Details associated with the embodiments described above and others are described below.

BRIEF DESCRIPTION OF THE DRAWINGS

The following drawings illustrate by way of example and not limitation. For the sake of brevity and clarity, every feature of a given structure is not always labeled in every figure in which that structure appears.

FIG. 7 is a partial sectional top view showing the clip-on cap in use according to one or more aspects of the disclosure.

DESCRIPTION OF ILLUSTRATIVE EMBODIMENTS

The present invention provides a portable, TRUS-integrated, FD-DOT for detection of aggressive prostate cancer. The invention improves the spatial resolution by coupling DOT with an ultrasound probe, which provides anatomical structures of the prostate so as to reduce the number of unknowns in the DOT image reconstruction by enabling correlation of ultrasound data with DOT data. While the combined TRUS-DOT method improves accuracy of reconstructed DOT images, that method relies highly on the ability of TRUS to locate the prostate cancer lesion. Given the fact that TRUS is unable to accurately detect prostate cancer and that to use TRUS to detect prostate cancer each region must be assumed to be homogenous, reconstructed DOT images using previous prostate cancer detection methods could be erroneous. To overcome this challenge, a hierarchical clustering method (HCM) can be used to improve the accuracy of image reconstruction with limited prior anatomical information.

EXAMPLES

Example 1

Design and Implement a TRUS-Integrated FD-DOT Optode Cap

The strength of DOT is to provide functional information about tumor physiology, but the weakness is lack of anatomical information. Since prostate cancer measurements are endoscopic, the lack of anatomical information to assist with locating suspicious regions is a weakness of DOT when used as diagnostic for PCa. This problem is overcome through combination of a clip-on cap that is capable of DOT and an ultrasound transducer. The advantage of the clip-on cap is twofold: (1) combination of the clip-on cap with the ultrasound transducer renders accurate and real-time anatomic information to correlate with data collected from a DOT optical system; and (2) the available anatomic information is used in the reconstruction algorithm to improve the algorithm's results. One design consideration for the clip-on cap is that it must be large enough to allow sufficient spacing between the light emitters and light detectors to permit light to pass through the human rectum and reach a depth of around 2 cm within prostate tissue, but without significantly increasing the diameter of the ultrasound transducer.

Figure 1:
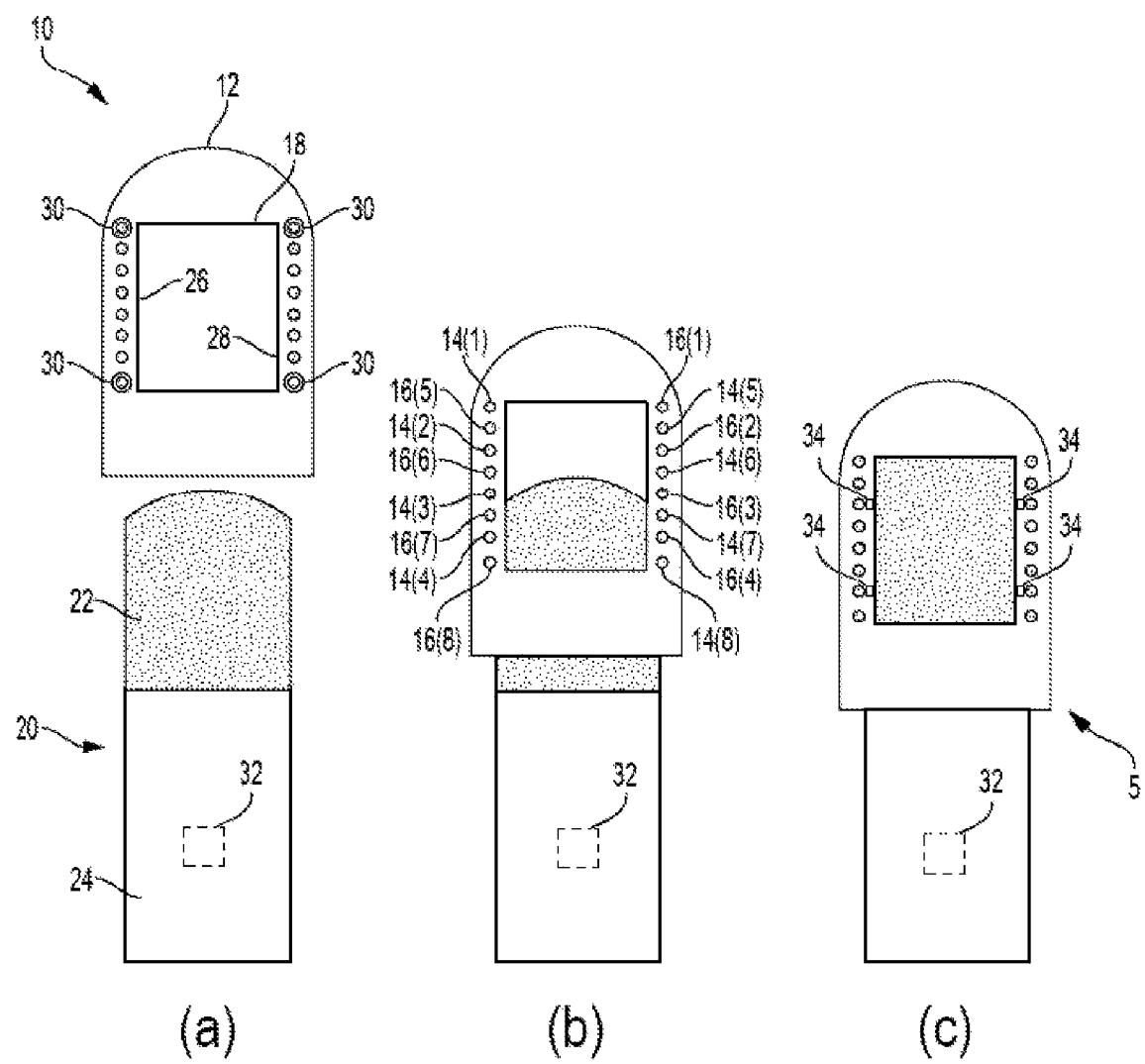
FIG. 1 is an elevation view of a TRUS-integrated clip-on cap according to one or more aspects of the disclosure.

Referring now to FIG. 1, an anomaly detection system 5 in accordance with one or more aspects of the disclosure is shown. The anomaly detection system 5 includes a clip-on cap 10 and an ultrasound transducer 20. The clip-on cap 10 comprises a hollow body 12, light emitters 14(1)-(8), light detectors 16(1)-(8), an ultrasound transducer window 18, and ultrasound fiducials 34. The anomaly detection system 5 also includes an ultrasound transducer probe 20 that comprises an ultrasound transducer 22, a probe body 24, and an accelerometer 32. The inner dimensions of the hollow body 12 are adapted to receive the ultrasound transducer 22. FIG. 1 shows: (a) the ultrasound transducer 20 separate from the clip-on cap 10; (b) the ultrasound transducer 20 partially inserted into the hollow body 12 of the clip-on cap 10; and (c) the ultrasound transducer 20 fully inserted into the hollow body 12 of the clip-on cap 10.

The clip-on cap 10 can comprise various styles and lengths to ensure compatibility with various ultrasound transducers, such as the BK® 8818 ultrasound transducer manufactured by BK Medical ApS. Furthermore, passing the probe through the rectum of a patient without local anesthesia brings extra challenges. For example, the probe needs to be soft for comfort and yet still be tolerant for all functions and operations of the light emitters 14(1)-(8) and light detectors 16(1)-(8) without reduction in quality. Various rubber-like materials are available to make the clip-on cap 10 be light-weight, thin-walled, soft, and smooth on an outer surface of the hollow body 12.

The clip-on cap 10 can be secured to the ultrasound transducer 22 in various ways, including, for example, clips, force fit, threaded connection, etc. When the ultrasound transducer 22 is inserted into the hollow body 12, the ultrasound transducer window 18 provides the ultrasound transducer 22 an unblocked line of sight through the hollow body 12.

The light emitters 14 and the light detectors 16 may comprise various optical emitters/sensors, such as optodes. Each light emitter 14 and light detector 16 is coupled to testing equipment by thin optical fibers (See FIG. 2). Use of thin optical fibers helps reduce an overall diameter of the clip-on cap 10. Limiting the diameter of the clip-on cap 10 is preferable because the nature of prostate cancer detection requires transrectal application of the probe. However, when the probe is to be used in conjunction with needle biopsy procedures, where local anesthesia and/or subject sedations are often introduced, the diameter of the TRUS probe is less of a concern.

The light emitters 14(1)-(4) are shown disposed along a first edge 26 of the ultrasound transducer window 18 and the light emitters 14(5)-(8) are shown disposed along a second edge 28 of the ultrasound transducer window 18. The light detectors 16(1)-(4) are oppositely disposed the light emitters 14(1)-(4) along the second edge 28, and the light detectors 16(5)-(8) are oppositely disposed the light emitters 14(5)-(8) along the first edge 26. This arrangement facilitates alternating matched pairs of light emitters 14 and light detectors 16. For example, the light detector 16(1) is paired with and detects light from the light emitter 14(1). Arranging pairs of light emitters 14 and light detectors 16 across the ultrasound transducer window 18 permits sufficient separation between the sensor pairs to interrogate deeper prostate tissues in a sagittal imaging geometry. Although the clip-on cap 10 of FIG. 1 includes eight sensor pairs, additional or fewer sensor pairs could be used depending on various design considerations. It is also noted that instead of alternating pairs, the light sensors 14(1)-(8) could each be disposed on either of first edge 26 or second edge 28. In a non-alternating arrangement, the light detectors 16(1)-(8) are disposed on the edge opposite the light emitters 14(1)-(8).

Figure 6:
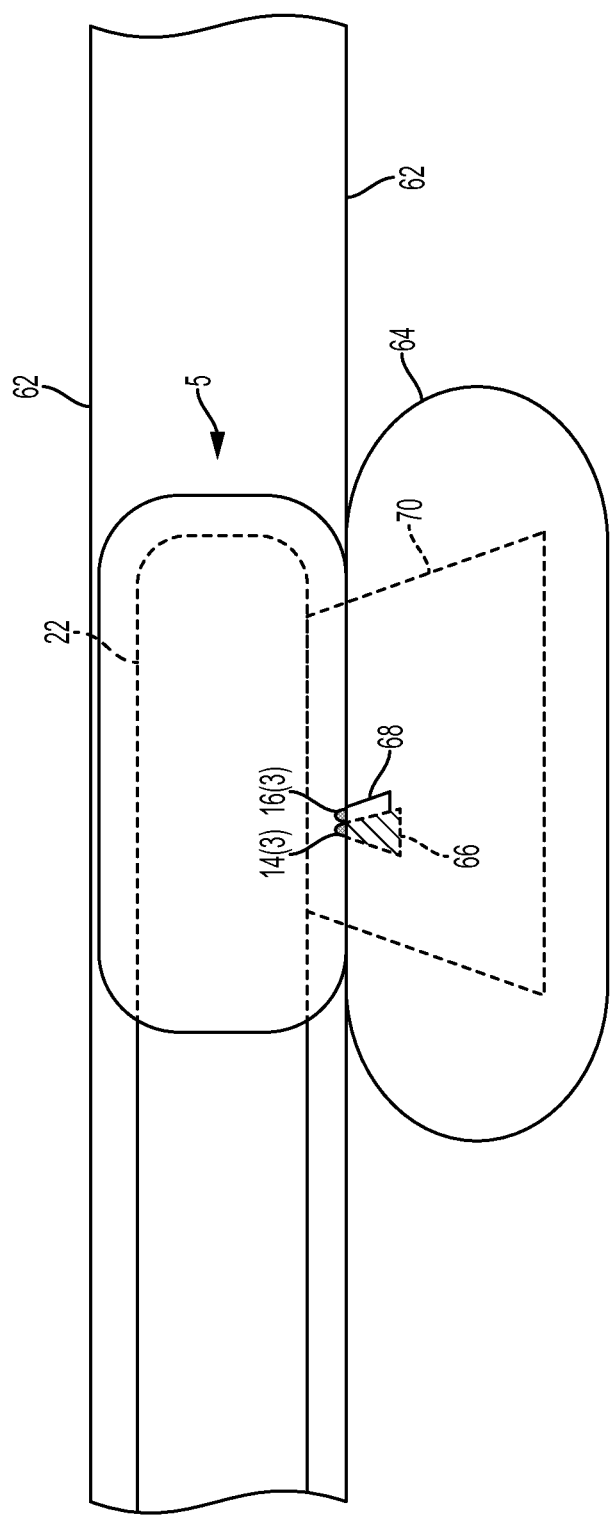
FIG. 6 is a partial sectional elevation view showing the clip-on cap in use according to one or more aspects of the disclosure.

Referring now to FIG. 6, a partial sectional view of the anomaly detection system 5 is shown in proximity to a prostate. The anomaly detection system 5 is shown abutting rectal walls 62, and in proximity to a prostate 64. As discussed above, a light emitter 14, for example light emitter 14(3) is adapted to project light 66 towards the prostate 64. Light 66 is shown represented as a cone. Some of light 66 that enters the prostate is scattered and a light detector 16, for example light detector 16(3), detects scattered light 68. Simultaneous to the light emission and detection, the ultrasound transducer 22 projects an ultrasound beam 70 towards the prostate 64.

Example 2

Design, Implement, and Test a Multi-Channel FD-DOT System

Figure 2:
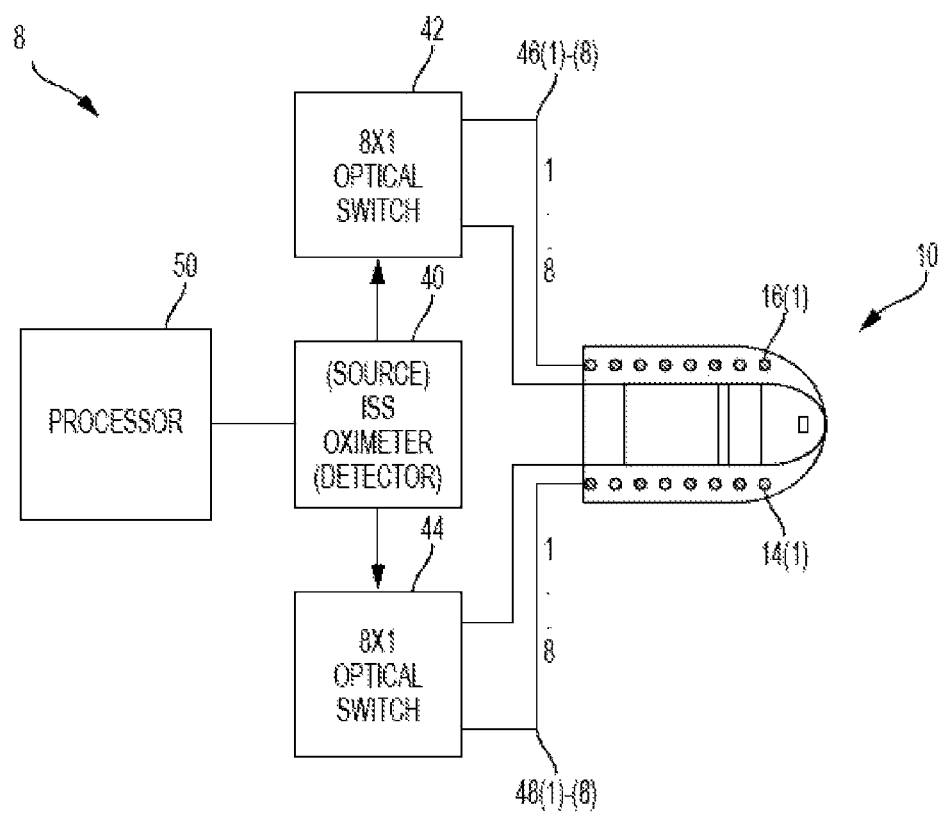
FIG. 2 is a schematic view of a clip-on cap according to one or more aspects of the disclosure.

Referring now to FIG. 2, a schematic view of a system 8 showing the clip-on cap 10 and associated hardware according to one or more aspects of the disclosure is shown. The system 8 includes an oximeter 40 is shown connected to a source optical switch 42, a detector optical switch 44, and a processor 50. Switches 42 and 44 enable the oximeter 40 to supply light to the light emitters 14 and receive light from the light detectors 16. The source optical switch 42 is coupled to the light emitters 14(1)-(8) of the clip-on cap 10 and provides switching to direct light from the oximeter 40 the light emitters 14(1)-(8) in sequence. The detector optical switch 44 is coordinated with the source optical switch 42 to collect detected light from the light detectors 16(1)-(8) in a matching sequence. Various optical switches are suitable, such as MEMS-based optical-switches manufactured by Sercalo Microtechnolgy, Ltd., Neuchatel, Switzerland. In aspects where only one light emitter 14 and one light detector 16 are used, the source optical switch 42 and the detector optical switch 44 may be omitted, in which case the light emitter 14 and the light detector 16 are coupled directly to the oximeter 40.

The oximeter 40 may be a dual-wavelength FD-oximeter, such as the OxiplexTS manufactured by ISS Medical, Champaign, IL This equipment is a FD-based non-invasive tissue oximeter for the determination of absolute values of HbO, HbR, and HbT, as well as light scattering at two wavelengths (690 nm and 830 nm). Using a FD-DOT system permits an independent quantification of light scattering from absorption. During operation of the anomaly detection system 5, the oximeter 40 includes two-wavelength diode lasers. Light emitted from the lasers is divided sequentially via the source optical switch 42 using time-division multiplexing. The divided light is then transmitted through optical fibers 46(1)-(8) to the light emitters 14(1)-(8), which causes the light to propagate through the prostate tissue. The light detectors 16(1)-(8) are synchronized with the light emitters 14(1)-(8) and transmit detected light to the detector optical switch 44 through optical fibers 48(1)-(8). The detected light is multiplexed by the detector optical switch 44 before being sent to a photomultiplier tube (PMT) inside the Oximeter 40. Analysis of the detected light may be performed by the oximeter 40, or by the processor 50. The processor 50 comprises various computer hardware adapted to receive and analyze data, and to carry out the various steps of a HCM 100 (see FIG. 3 and related discussion).

Calibration of the anomaly detection system 5 can be performed in the following manner. A homogeneous liquid tissue-mimicking phantom is prepared using blood mixtures with intralipid solution. One liter of 1% intralipid solution is made so that the analytical diffusion solutions can be applied. Multiples of 10 ml of animal blood will be added into the solution and mixed thoroughly. A co-oximeter will be used to measure Hb, HbO, HbT concentrations, and hemoglobin oxygen saturation ($SO_2$) of the animal blood before the animal blood is added into the solution. To deoxygenate the animal blood mixture, a non-oxygen gas, such as $N_2$, is bubbled through the mixture. To oxygenate the blood mixture, pure $O_2$ gas is bubbled through the mixture. An additional oximeter is used as a reference to provide needed optical parameters. The multiplexed optical source and detector filers from the newly made FD-DOT system are placed on the side of a container containing the liquid tissue-mimicking phantom. The values of HbR, HbO, and $SO_2$ for each of several combinations of 3-sources-and-1-detector clusters (which are needed in order to calculate HbR, HbO, and $So_2$ based on FD-NIRS) can then be measured and compared with expected values obtained from the co-oximeter and another independent oximeter. If the results from FD-DOT and the expected values are within 90% of one another, the performance of FD-DOT is acceptable. If the results vary by more than 10%, refinement of the system implementation may be needed. For example, both electrical and optical connections should be carefully checked and improved.

A reliability assessment using intraclass correlation coefficient of the anomaly detection system 5 can be performed in the following manner. The intraclass correlation coefficient (ICC) is calculated using the collected $\mu_s'$ values to assess the reliability of ED-DOT in measuring optical properties of tissue samples. ICCs are popular reliability measures which have been widely used to assess the reliability of imaging techniques, such as for NIRS [23,24] and MRI [23,25-27]. For the reliability assessment, phantom data is analyzed. An assessment of human prostate data measurements can be performed later. Several types of ICCs are available, depending on the ANOVA model of the data. Since the effect of measurement is the major factor to consider here, a one-factor random-effect model is appropriate for the phantom data, and thus the following ICCs will be used [28,29] where ICC(1,1) is for single measurement and ICC(1,k) is for the average of k repeated measurements at each measurement site. "MS(Specimen)" and "MS(Error)" are the between-specimen mean squares and error mean squares, respectively, which can be obtained by SAS. The ICC(1,1) and ICC(1,k) are calculated for both $\mu_a$ and $\mu_s'$ values (See Equation 1 and Equation 2 below). Values of the FD-DOT of ICC(1,1)>0.8 and ICC(1,k)>0.9 indicate an acceptable reliability. Otherwise, refinement of both electrical and optical connections should be carefully analyzed and improved.

$$ICC(1,1) = \frac{MS(\text{Specimen}) - MS(\text{Error})}{MS(\text{Specimen}) + 4MS(\text{Error})} \quad \text{Eq. 1}$$

$$ICC(1,k) = \frac{MS(\text{Specimen}) - MS(\text{Error})}{MS(\text{Specimen})} \quad \text{Eq. 2}$$

Example 3

Integrate the New FD-DOT System with the Clip-On Cap for Further System Testing and Calibration, Followed by Reliability Analysis and Removal of Possible Sources of Noise Example 3 is performed for ED-DOT system testing without using the clip-on cap 10. After all the optical fibers 46(1)-(8) and 48(1)-(8) are packed and confined within the hollow body 12, it is necessary to further test and recalibrate the anomaly detection system 5 and to quantify the reliability of the anomaly detection system 5. These tests can be performed by clamping the clip-on cap 10 in contact with an intralipid tissue phantom. The same experimental protocols and test-retest assessment analysis discussed above is repeated. The passing conditions remain the same. 90% agreement between the results derived from FD-DOT and the expected values for both $\mu_a$ and $\mu_s'$; and ICC(1,1)>0.8 and ICC(1,k)>0.9 for both $\mu_a$ and $\mu_s'$.

Example 4

Trans-Rectal DOT Image Reconstruction by HCM with Limited Prior Information

Figure 3:
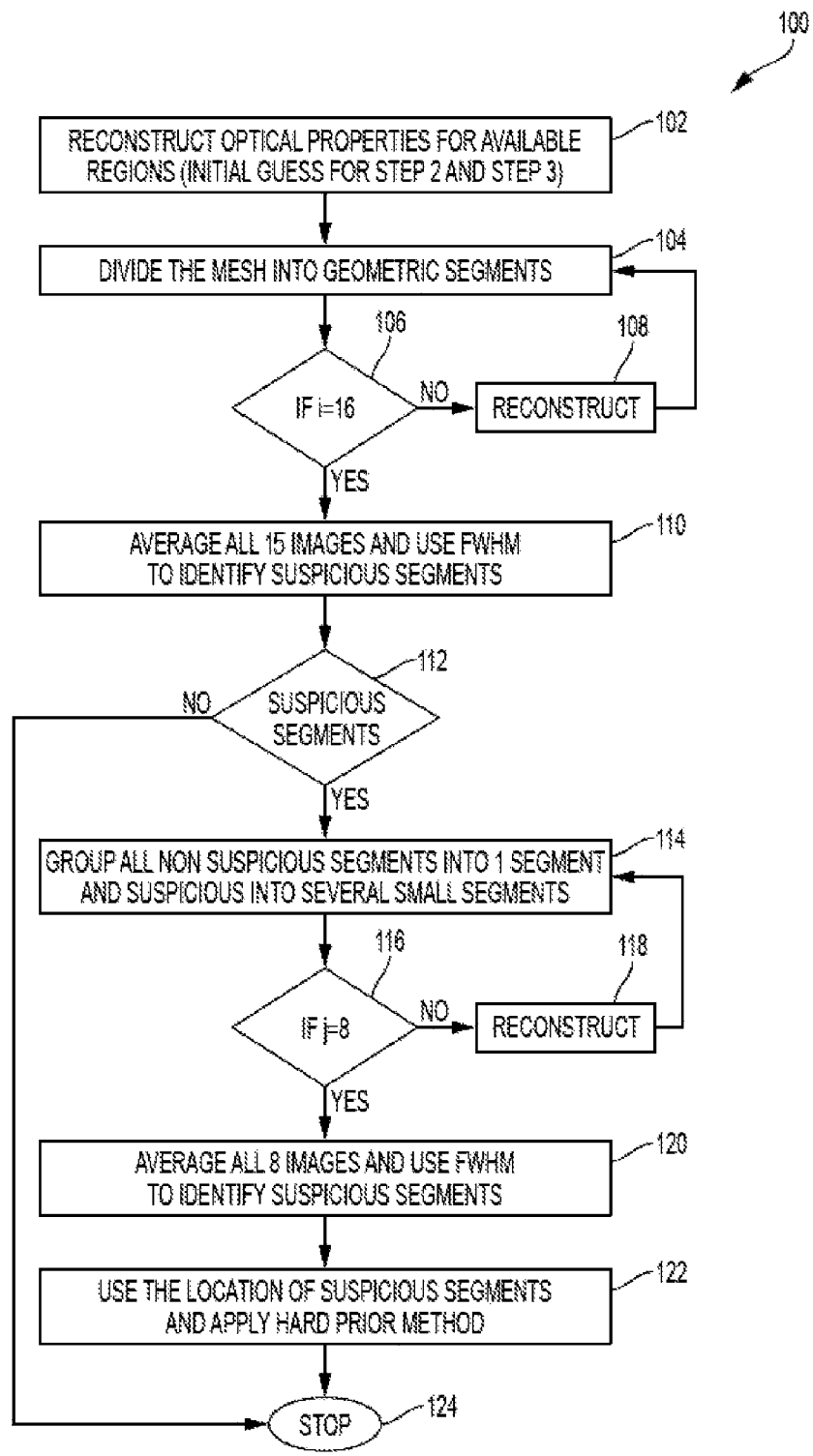
FIG. 3 is a flow diagram of a method of detecting sub-surface anomalies according to one or more aspects of the disclosure.

Referring now to FIG. 3, a hierarchical clustering method 100 using the anomaly detection system 5 is shown. The HCM 100 can be used to reduce a parameter space by segmenting the medium or region of interest (ROI) into several geometric units or clusters (e.g., See FIG. 5). It is assumed that each of the geometric clusters is homogeneous and has the same optical property. By limiting the assumption of homogeneity to subsets of the parameter space, the medium or image domain can be partially heterogeneous since the domain may contain several geometric clusters of different homogeneity. During the DOT image reconstruction process, a value of $\mu_a$ or $\mu_s'$ or both from each cluster is updated as the data is collected by the anomaly detection system 5. Since the size of each cluster is user-defined, the smallest cluster can be a single finite element method (FEM) mesh node and the largest can be the entire domain region, similar to that used in the regular reconstruction method without any spatial prior.

The Levenberg-Marquardt (LM) algorithm is widely used to reconstruct absolute optical properties ($\mu_a$ and $\mu_s'$) in DOT used for FD and CW cases. The limitation of LM is to get trapped in a local minimum which is close to the initial guess. An algorithm that can provide global optimization is needed. The simulated annealing (SA) algorithm, a global optimization technique, has been also used widely in other areas of optimization and explored in the field of biomedical optics. However, SA has a limitation of slow convergence. In order to rectify the shortcoming of both techniques, a hybrid reconstruction technique was used to isolate the final image from initial guess and speed up the reconstruction.

To validate the HCM 100, a simulated TRUS-DOT probe was used having 16 co-located or bifurcated optodes that served as both sources and detectors. Computer simulations were performed by considering a FEM mesh, which was created to be anatomically similar to a TRUS image of a human prostate. The FEM mesh consisted of four ROIs: prostate tissue, peri-prostate tissue, rectum wall tissue, and a prostatic tumor (anomaly). The FEM mesh used in this study was an unstructured tetrahedral mesh with 28,174 nodes and 156,191 elements. The thickness of the rectum wall was set to be 5 mm with a curvature radius of 50 mm.

The following optical property (i.e., absorption coefficient) distributions were used: 0.01 mm$^{-1}$ for rectum wall, 0.002 mm$^{-1}$ for surrounding tissue, 0.006 mm$^{-1}$ for prostate, and 0.02 mm$^{-1}$ for anomaly. An anomaly was created at 1-cm depth from the rectum wall to test the HCM 100. The CW mode was utilized in the simulations, and 1% random noise was added to the data to mimic the instrument noise.

Figure 4:
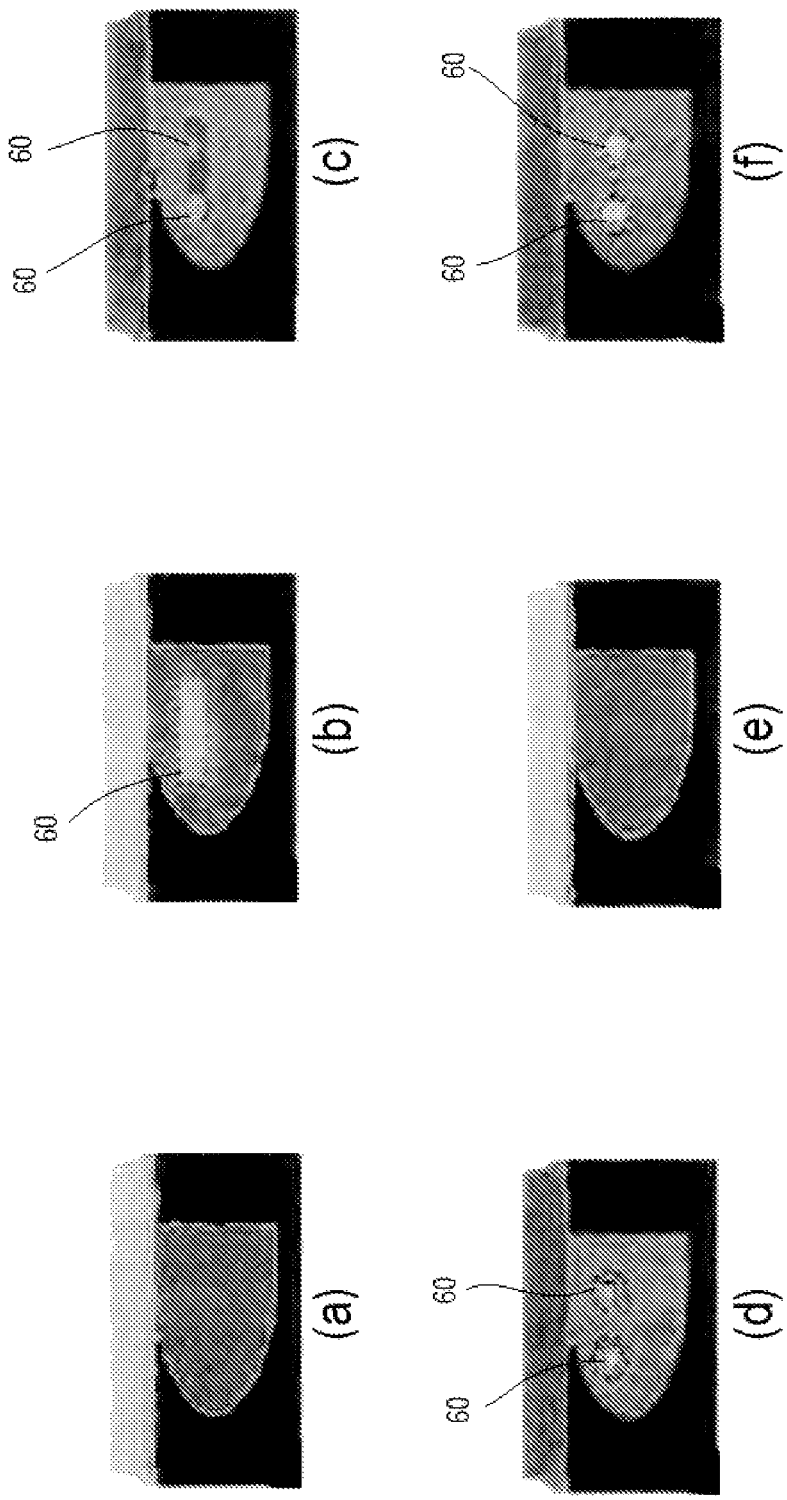
FIG. 4 depicts panels resulting from various steps of the method of detecting sub-surface anomalies according to one or more aspects of the disclosure.

Simulated DOT data was computed using the diffusion forward model with FEM, and NIRFAST was used to perform the forward calculation. The HCM 100 was used to reconstruct images from all simulated data. Referring now to FIG. 3 specifically, a flow chart demonstrating the HCM 100 is shown. The method 100 begins at step 102 where ultrasound data regarding a region of interest may be collected and optical properties of various anatomical features are reconstructed using initial guesses for light absorption of anatomical features, such as the rectum wall, surrounding tissue, prostate tissue, and anomalies. For example, an absorption coefficient with a value of $\mu_a$=0.01 mm$^{-1}$ is initially assumed to recover the optical properties of the rectum wall, prostate, and surrounding tissue. The reconstructed data from step 102 serves as a starting point upon which subsequent steps build upon to perform the rest of the analysis. FIG. 4(*a*) depicts an exemplary panel resulting from step 102. FIG. 4(*a*) shows an initial assumption of $\mu_a$=0.01.

Figure 5:
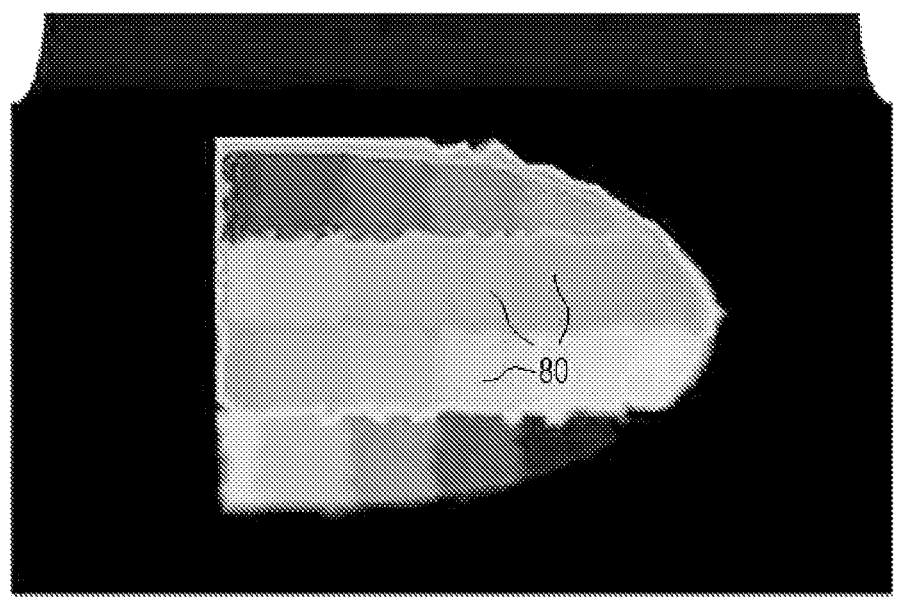
FIG. 5 is a panel depicting geometric clusters created by the method of detecting sub-surface anomalies according to one or more aspects of the disclosure.

At step 104 the prostate region is divided into several geometric clusters. FIG. 5 demonstrates exemplary geometric clusters 80. According to various aspects, each geometric cluster 80 can have a tissue volume of, for example, 1.00 to 8 cm$^3$. The method 100 then proceeds to step 106 to confirm whether or not the number of clusters created is equal to 16. If 16 clusters were not created, the method 100 proceeds to step 108 where another reconstruction is performed. The number of clusters created by the HCM 100 is an iterative process that is described in more detail in the Methods section herein below. After step 108 is completed, the method 100 returns to step 104. This process may be iterated until the number of clusters generated is equal to 16. When the number of clusters is equal to 16, the method 100 proceeds to step 110.

At step 110, an average absorptivity of the 16 images is calculated and suspicious regions are identified using full width half maximum (FWHM) analysis. The FWHM analysis identifies suspicious segments 60 in the tested area by identifying areas exhibiting high light scatter. Areas of high light scatter can be seen in FIG. 4(*b*) as a lighter colored area in the shape of a rectangle. FIG. 4(*b*) is an example of a result from step 110. Because of the different optical properties of tissues containing PCa, areas of high light scatter identify anomalies within the prostate that may indicate PCa. The method 100 then proceeds to step 112 to evaluate whether any areas of high light scatter were located. If no such areas are located, the method 100 proceeds to step 124 and the method 100 ends. If no areas of high light scatter are located, the presence of PCa in the tested area is unlikely. If areas of high light scatter are located at step 112, the method 100 proceeds to step 114.

At step 114, the geometric clusters 80 that were created in step 104 that contain suspicious segments 60 are further divided into smaller clusters having a tissue volume of, for example, 0.125-0.42 cm$^3$. The remaining non-suspicious segments can be grouped into one segment. The method 100 then proceeds to step 116 to confirm whether or not the number of smaller clusters created is equal to eight. When the number of clusters created is equal to eight, the method 100 proceeds to step 118 where another reconstruction is performed. After step 118 is completed, the method 100 returns to step 114. This process may be iterated until the number of clusters generated is equal to eight. When the number of clusters is equal to eight, the method 100 proceeds to step 120.

At step 120, an average absorptivity of the seven smaller clusters using FWHM is calculated to refine the location of the anomalies. Recalculation of the FWHM of the images refines the location of the anomalies by essentially increasing the resolution of the suspicious segments 60. FIG. 4(*c*) is an example of a result from step 120. As shown in the FIG. 4(*c*), the $\mu_a$ value of the anomalies within the suspicious segments 60 has been improved compared to FIG. 4(*b*). In FIG. 4(*c*), it begins to become apparent that there are two separate anomalies within the suspicious segments 60. The method 100 then proceeds to step 122.

At step 122, further reconstruction is used to provide an updated location of anomalies that were detected through application of the method 100. FIG. 4(*d*) is an example of a result from step 122. After step 122 of the HCM 100, FIG. 4(*d*) the $\mu_a$ value of the anomalies has again been improved, more clearly illustrating the location of two anomalies in two separate suspicious segments 60. The method 100 then ends at step 124. Now that the location of anomalies has been determined, the appropriate treatment steps can be carried out. For example, biopsy of the areas containing the anomalies may be performed to investigate the possibility of PCa.

The panels in FIG. 4 provide an example of overall comparisons among the reconstructed images for two targeted tumor lesions through computer simulations. FIG. 4(*a*) depicts the HCM 100 after step 102. FIG. 4(*b*) depicts the HCM after step 110, where the lighter colored rectangle indicates a location of suspicious segments 60 selected using full width half maximum (FWHM). FIG. 4(*c*) depicts the HCM 100 after step 120, where the lighter colored spots indicate locations of two suspicious segments 60. FIG. 4(*d*) depicts the HCM 100 after step 122, where the location of the suspicious segments 60 has become a bit more visible. FIG. 4(*e*) depicts a reconstructed image without any inclusions, but reconstructed using the HCM 100. FIG. 4(*f*) displays a reconstructed image for the same two-inclusions case using known anatomical information for inclusions. Note that the anatomical prior information used does not include the cancer/tumor locations, which were needed for the method.

Example 5

Trans-Rectal DOT Image Reconstruction by HCM with Two Absorbers

The capability of differentiating two absorbers by the HCM 100 is important in prostate cancer imaging because of the existence of multifocal cancer regions. An investigation of the ability of the HCM 100 to reconstruct two absorbers within a tissue was performed. Two cases were investigated. In Case 1, two anomalies of 1-cm diameter were created at the depth of 2 cm from the surface. The two anomalies were separated by 2 cm. This test was useful in understanding the minimum separation between two absorbers that is required to recover them as two separable absorbers in reconstructed images. Case 1 also allowed an estimation of the recovery of off-centered absorbers. This estimation is important because the sensitivity of DOT is often higher in the center of the image domain due to the number of overlapping measurements. In Case 2, the absorbers were created at the depths of 1 cm and 2 cm, respectively. The horizontal separation between the two absorbers was increased to 4 cm. In both cases, the HCM 100 was able to successfully determine the locations of the anomalies.

Example 6

Investigation of HCM on Effects of Different Background (Prostate Region) Contrast Further investigation of the HCM 100 on variation of background absorption in the prostate region is helpful to understand and estimate effects of the background optical properties on the reconstructed DOT images. As explained above, Steps 104, 106, and 110 of the HCM 100, an overall area of the anomaly was identified by selecting the FWHM of the recovered optical properties. If the recovered optical properties were not much higher than that of the background, no probable anomaly would be identified. Therefore, the background absorption or contrast plays an important role in achieving high-quality DOT images of prostate cancer. To estimate effects of the background optical properties, 11 simulations were performed by varying the optical properties or $\mu_a$ values of the prostate (i.e., background tissue) from 0.005 to 0.015 mm$^{-1}$. The absorption coefficients for the surrounding tissue and the rectum wall were fixed; the anomaly contrast was set to be three times greater than the background (0.015 to 0.045 mm$^{-1}$) in all the simulations. The reconstructed results were plotted by comparing the recovered optical properties to the background, which showed the recovered contrast from the background after steps 104, 106, and 110 using the HCM 100. A recovery rate (RR) was also calculated based on the recovered absorption (RA) versus expected absorption (EA) as expressed by RR=(RA/EA)*100. Specifically, the calculations gave rise to an averaged RR of 40% over all 11 simulations. This 40% recovery rate of the expected contrast indicates that variations in background optical properties would still allow the probable location of an anomaly in steps 104, 106, and 110 to be located as long as the absorption contrast between the anomaly and background is 3 times greater.

The reason the test was stopped at steps 104, 106, and 110 was that this stage of the HCM 100 is crucial for the success of the algorithm. If enough contrast in absorption was obtained with respect to the background in this step, the HCM 100 would be able to identify the region of interest for possible cancer lesions. Further steps (i.e., steps 114, 120, and 122) allow refinement of the size, location, and optical properties to achieve final reconstructed images with high quality. If the HCM 100 failed to recover a reasonable amount of contrast in steps 104, 106, and 110, then the HCM 100 would fail to give rise to correct results. Indeed, this is a difference between the approach described herein and those approaches of previous researchers.

Example 7

Developing a Co-Registration Method to Landmark the Prostate During Surgery

Referring now to FIG. 7, a top down view of the anomaly detection system 5 is shown in proximity to the prostate 64. As shown in FIG. 7, the anomaly detection system 5 is shown in three positions, demonstrating how the ultrasound transducer 22 of the anomaly detection system 5 can scan the prostate 64. The clip-on cap 10 is shown in contact with rectal wall 62. As the anomaly detection system 5 rotates from (a) to (b) to (c), the ultrasound transducer 22 projects the ultrasound beam 70 towards the prostate 64. In order to reconstruct data from the ultrasound transducer 22 and the clip-on cap 10, both data sets need to be co-registered with the prostate 64. The ultrasound and optical data sets can be combined and related to one another to provide location information relative to the prostate 64. Combination of the data sets can be accomplished in the following manner. First, several 2D ultrasound axial scans of the prostate 64 are acquired by rotating the anomaly detection system 5 from side to side (See (a), (b), and (c) of FIG. 7). The acquired images are used to create a 3D mesh, which is utilized in the HCM image reconstruction as prior/known anatomical information. Next, the geometric relationship between the 2D ultrasound images and 3D optical images is established by incorporating two accessories on the probe. The first accessory comprises four ultrasound fiducials 34 (see FIG. 1) that are placed on an outer surface of the hollow body 12 of the clip-on cap 10, each of which is adjacent to a light emitter 14 or a light detector 16. The fiducials 34 provide a known reference point that is used to correlate the ultrasound data with the optical data. Location information for the light emitters 14 and light detectors 16 that are not adjacent to one of the fiducials 34 can be calculated since geometry of the clip-on cap 10 is fixed. Alternatively, additional fiducials 34 can be included as reference points for additional light emitters 14 and light detectors 16.

The second accessory comprises an accelerometer 32 that is associated with the anomaly detection system 5. For example, as shown in FIG. 1, the accelerometer 32 can be disposed within the probe body 24. Because examination of the prostate 64 is endoscopic, orientation of the ultrasound transducer 24 and the clip-on cap 10 cannot be easily tracked. Not knowing the orientation of the ultrasound transducer 24 and the clip-on cap 10 can lead to errors in location information, which in turn leads to erroneous image reconstruction. The accelerometer 32 helps overcome this problem by providing information regarding orientation of the ultrasound transducer 24 and the clip-on cap 10. For example, an accelerometer 32 can provide information regarding pitch, yaw, and roll. Various accelerometers may be used, such as the ADIS16400, manufactured by Analog Devices, Inc. Information from the accelerometer 32 can be used to determine the orientation of ultrasound data collected by the ultrasound transducer 22 with respect to optical data collected by the light detectors 16, which enables a user to identify locations of any detected anomalies within the prostate 64.

Example 8

Performing TRUS/FD-DOI Measurements from In Vivo Human Prostate Glands, During Prostatectomy FD-DOI measurements are taken from human prostate glands in vivo during prostatectomy. In this case, the clip-on cap 10 will be sterilized as a conventional TRUS probe right before the prostatectomy, but after the patient is under anesthesia. The FD-DOI measurement locations will be co-registered with a clinical TRUS device for later comparison and validation. Five optical scans are taken at different anatomical positions. The corresponding images will be collected and stored for later analysis.

Image reconstruction and analysis is performed using LM-SA and the HCM 100 on in vivo human prostates. Similarly, both light scattering and HbO/HbR images will be obtained in order to examine whether or not hemoglobin concentrations are significantly different between high-grade and low-grade PCa, as well as light scattering properties. Both of the reconstructed images will be confirmed by whole-mount histology analysis; corresponding sensitivity and specificity will be also quantified.

DOI measurements are very sensitive to optical interface between the optodes and tissues. It is very critical to ensure sufficient contact or good optical coupling. However, as the examination is endoscopic, it is difficult to know if the optodes (e.g., the light emitters 14 and the light detectors 16) are in sufficient contact with the optical interface because the user cannot see the optodes. To address this problem, capacitive-based touch sensors can be included on the clip-on cap 10. FIG. 1 shows touch-sensitive electrodes 30 disposed around optodes of the clip-on cap 10. As shown in FIG. 1, four touch-sensitive electrodes 30 are disposed on the clip-on cap 10. Alternatively, more or fewer touch-sensitive electrodes 30 can be included as desired. Various touch-sensitive electrodes can be used. In one or more aspects, the touch-sensitive electrodes 30 may be copper pads.

A touch-sensitive area is created by incorporating, for example, copper pads around one or more of the light emitters 14 and the light detectors 16. The copper pads will then be connected to capacitive sensing-controller input pins with traces underneath the probe. When the copper pads are not in contact with a tissue, the capacitive sensing controller measures parasitic capacitance (PC) which is the sum of the distributed capacitance on the copper pads. When the probe is in good contact with the rectum, the copper pads will form a simple parallel plate capacitor with capacitance RC. The total sensor capacitance (SC) becomes SC=PC+RC. The capacitive sensing controller monitors the sensor capacitance by converting the measured capacitance into a digital value which will be read by a computer. A LED-based indicator can be created using Labview software so that a user is notified when had optical coupling conditions exist. The position of the probe can then be adjusted based on the LED status.

Methods

Forward and inverse methods in DOT. Light transport in biological tissues can be modeled by the diffusion approximation (DE) to the radiative transport equation (RTE), assuming that light scattering has great effects on light propagation in tissue. In the frequency domain, the diffusion equation is given by $$-\nabla D(\vec{r})\nabla \Phi(\vec{r},\omega)+(\mu_a(\vec{r})+i\omega/c)\Phi(\vec{r},\omega)=Q_0(\vec{r},\omega)$$ Eq. 1 where $\Phi(\vec{r}, \omega)$ is the photon density at the position $\vec{r}$, $\omega$ is the modulation frequency of light (in this study a CW domain was used, so $\omega=0$), $Q_0(\vec{r}, \omega)$ represents the isotropic source, c is the speed of light in the medium and $\mu_a$ is the absorption coefficient; finally, $D(\vec{r})$ is the optical diffusion coefficient which is defined as:

$$D(\vec{r})=1/3[\mu_a(\vec{r})+\mu_s'(\vec{r})]$$ Eq. 2

Where $\mu_s'(\vec{r})$ is the reduced scattering coefficient and is defined as $\mu_s'(\vec{r})=\mu_s(\vec{r})(1-g)$. Here $\mu_s(\vec{r})$ is the scattering coefficient and g is the anisotropic factor. Equation (1) can be solved using the finite element method (FEM) and applying Robin-type (30) (known as type III or mixed) boundary condition to model the refractive index mismatch at the boundary.

For a CW system, measurements are only amplitudes of light intensities and are used to estimate the spatial distribution of the product of $\mu_a(\vec{r})$ and $\mu_s'(\vec{r})$, namely, $\mu_{eff}(\vec{r})=\mu_a(\vec{r})\mu_s'(\vec{r})$, or the distribution of $\mu_a(\vec{r})$ if $\mu_s'(\vec{r})$ is known and homogeneous. It is known that $\mu_{eff}(\vec{r})$ values of prostate cancer are different from those of normal prostate tissues. Based on previous knowledge learned from breast cancer detection and diagnosis with DOT, this study was started with an assumption that light absorption $\mu_a(\vec{r})$ is the major source for optical contrast between cancerous and normal prostate tissues, while changes in $\mu_s'(\vec{r})$ induced by prostate cancer are much less significant. Accordingly, the aim of the DOT reconstruction in this paper is to recover the light absorption property, $\mu_a(\vec{r})$, from NIR measurements taken on the boundaries. The objective function, $\Omega$, for this procedure can be written as $$\Omega =_{D,\mu_a}{}^{min}\{\|y-F(D,\mu_a)\|^2+\lambda\|(D,\mu_a)-(D,\mu_{a0})\|^2\}$$ Eq. 3

Where y is a matrix to express all the measured data, F is the forward-calculation operator (or matrix) that generates diffusion-based light propagation responses, $\|\cdot\|^2$ is the L2 norm, $\lambda$ is the regularization parameter and $\mu_{a0}$ is the initial estimate of light absorption coefficient. Note that variables D, $\mu_a$ and $\mu_{a0}$ are simplified notations for $D(\vec{r})$, $\mu_a(\vec{r})$, and $\mu_{a0}(\vec{r})$, respectively. By minimizing Eq. (3), which is achieved by setting the first derivative of Eq. (3) with respect to $\mu_a$ as zero following a Taylor series, and ignoring the $2^{nd}$ and higher order terms, the following updated equation is arrived at:

$$(J^TJ+\lambda I)(\delta\mu_a)=J^T[y-F(\mu_a)]+\lambda[(D,\mu_a)-(D,\mu_{a0})]$$ Eq. 4

Where J is the Jacobian matrix, I is the identity matrix, and $\delta\mu_a$ ($\delta\mu_a=\mu_a-\mu_{a0}$) is a spatial distribution matrix of changes in $\mu_a$ with respect to the initial given value. Note that $\mu_{a0}$ is only the initial estimate at the first iteration. After the first iteration, $\mu_{a0}$ is basically the previous estimate. Now Eq. (4) becomes Eq. (5) after $\mu_a-\mu_{a0}$ is replaced by $\delta\mu_a$, $$(J^TJ+2\lambda I)(\delta\mu_a)=J^T(y-F(\mu_a)).$$ Eq. 5

As mentioned earlier, only changes in $\mu_a$ were considered here, because the DOT measurement utilizes CW NIR light with an assumption that variation in light scattering across the medium is minimal Specifically, a uniform distribution of $\mu_s'(\vec{r})=10$ cm$^{-1}$ was utilized across different prostate tissue regions in all simulation examples to be shown in Section 3. Then, further discussion can be had regarding how to remove or modify this assumption in Section 4.

Hierarchical clustering. In the HCM 100, the reduction of a parameter space is realized by segmenting the medium or region of interest (ROI) into several geometric units or clusters. Each of the geometric clusters was assumed to be homogeneous and to have the same optical property. In this way, the medium or image domain could be partially heterogeneous since the domain may contain several geometric clusters. During the DOT image reconstruction process, a value of $\mu_a$ from each cluster was updated using Eqs. (3) to (5). Since the size of each cluster was user-defined, the smallest could be a single FEM mesh node and the largest could be the entire domain region—similar to that used in the regular reconstruction method without any spatial prior. Specifically, the nodes in the mesh were tagged and separated into clusters, as indicated by $c_1, c_2 \ldots c_j$ with respect to each cluster. The Jacobian matrix in Eq. (5) was then modified to be J* as given by:

$$J^* = JC, \qquad \text{Eq. 6}$$

Where matrix C had the size of NN×NC (number of nodes×number of clusters). The elements of matrix C were given as follows:

$$C(i, j) = \begin{Bmatrix} 1 & \text{if } i \in c_j \\ 0 & \text{else} \end{Bmatrix} \qquad \text{Eq. 7}$$

Where i marks the number of nodes and j labels the number of clusters. By the end of each iteration, the solution vector of $\delta\mu_a$ was mapped back to each node using Eq. (8), $$\delta\mu_a = C(\delta\mu_a^*) \qquad \text{Eq. 8}$$

Where $\delta\mu_a^*$ is the vector with optical properties in respective geometric clusters solved from Eq. (5). The function of matrix C is to transform the initial image domain into a new image domain where the inverse procedure is performed with cluster-based geometric structures. Matrix C is a mediator or operator that converts the regular geometry to and from cluster-based geometry for the reconstructed object. So, technically no inversion or transpose of C is directly involved.

Initially, two ROIs were reconstructed, such as background and an anomaly; the background mesh was geometrically segmented in a heterogeneous fashion. For multiple ROIs, the proposed method was hierarchically implemented by segmenting the region which was more prone to cancer, while utilizing available prior information. Specifically, the proposed method was implemented in multiple steps, as shown in FIG. 3. To image prostate cancer through trans-rectal DOT imaging, four types of tissues were examined: rectum wall, peri-prostate tissue, prostate and tumor. Each of these tissues has its own optical properties. When being imaged without any prior anatomic information, different types of tissues are highly likely to be mixed among one another because their optical contrasts are relatively subtle, and it is difficult to distinctly separate them. Thus, in the HCM described herein, it is desirable to achieve an improved spatial resolution for prostate imaging.

In step 102 of the HCM 100, reconstruction was performed based on prostate anatomic images offered by TRUS and the assumption of a homogeneous prostate. With such hard prior spatial information collected, the reconstructed $\mu_a$ values in both background and prostate regions (as two ROIs) should be reasonably accurate with respect to the actual values, assuming that the sizes of the prostate tumors are much smaller than the size of the prostate. Then, the reconstructed $\mu_a$ values in available ROIs would serve as the initial guess in steps 104 and 114.

Steps 104, 106, 108, 110, and 112 of the HCM 100 were dedicated to finding the probable locations of anomalies (i.e., prostate tumors). To achieve this, the prostate region was geometrically divided into several clusters, so that the prostate tissue became a heterogeneous medium (e.g., See FIG. 5). However, without prior knowledge of suspicious locations, dividing the prostate into several clusters or elements may result in a mixing of suspicious tissue with normal prostate tissue and vice versa. In order to prevent mixing, a hierarchical approach was used to cluster the prostate volume with different unit volume sizes in an iteratively manner to minimize the mixing effect of cancer and normal tissues within a cluster.

Specifically, the initial volume of a cluster was chosen to be 1×1×1 cm³. Then, the volume of the cluster was varied by increasing the length of the cluster in each of the x, y, and z dimensions iteratively. For example, an increase in length of 0.5 cm in only the x direction gave rise to a unit volume of 1.5×1×1 cm³, followed by the same length increase in only y or only z direction. In this way, eight different unit volumes in three x, y, z directions were generated by increasing the linear length in only one dimension (x, y, z), or in two dimensions (xy, yz, xz), or in three dimensions (xyz). The procedure is given as follows: (1) reconstruct an initial $\mu_a$ image with a starting base unit size (i.e., 1×1×1 cm³), (2) save the reconstructed image, and go back and change the unit volume size (e.g., 1.5×1×1 cm³ or 1.5×1.5×1 cm³ or 1.5×1.5×1.5 cm³) and reconstruct the image again (step 104 in FIG. 3). To be more comprehensive, the base unit volume was increased from 1×1×1 cm³ to 1.5×1.5×1.5 cm³. A length interval of 0.5 cm was then applied to increase the base unit (e.g., 2×1.5×1.5 cm³, 2×2×1.5 cm³, or 2×2×2 cm³). In this way, another set of eight reconstructed images were generated with varied base unit volumes resulting in an overall 16 (i=16) images (resulting from 16 combinations) by the end of step 112. (3) All of the reconstructed $\mu_a$ images were averaged to obtain the final image. (4) Next, suspicious clusters that have high $\mu_a$ values with respect to the background were searched for. Such clusters that have high $\mu_a$ values indicate the possibility of cancer. Specifically, the location of suspicious clusters was selected using full width half maximum (FWHM) of the updated $\mu_a$ values within the prostate region. If no suspicious cluster were identified, the conclusion is that the prostate has a low probability of having cancer.

In step 114, if some suspicious clusters in step 112 are seen, all of the non-suspicious clusters are grouped as one new single cluster, and the suspicious clusters are divided into further smaller clusters. Next, an initial unit volume size used within the suspicious regions is set to be 0.5×0.5×0.5 cm³. The procedure explained above is repeated here with a length variation of 0.25 cm in any one of three dimensions. Similar to step 104, the final reconstructed image of Step 3 is an average of eight images (j=8) that are obtained by varying the unit volume in eight different fashions. FWHM of the $\mu_a$ values is still used to localize suspicious regions for further inspection with an improved spatial resolution.

The HCM 100 utilizes a region-specific regularization parameter to favor reconstruction in the prostate region using a hierarchical approach. The underlying rationale of this approach was previously discussed where the regularization parameter controls the level of optical property updates at each iteration. A larger regularization parameter gives rise to a subtle update, while a smaller regularization parameter offers a steeper update with a broader solution range. A smaller regularization value applied to the prostate region permits the HCM 100 to focus only on the prostate and to accurately update the reconstructed optical properties of the prostate. Finally, in step 122, the reconstruction process is repeated using the suspicious regions identified in previous steps as hard prior anatomy or as given cancer regions, with a uniform initial guess as used in step 102.

In principle, selections of regularization parameters and stopping criterion play a key role in any iteration-based reconstruction techniques. For the various iterative steps of the HCM 100, the number of iterations was empirically determined. For step 102, the regularization parameter was 10 and the stopping criterion was indicated when the change in projection error was less than 2% of that in the previous iteration. For steps 104, 106, and 108, the regularization parameter was 0.1, and the stopping criterion was indicated when the change in projection error was less than 20% of the previous iteration. The reason for this criterion at steps 104, 106, and 108 was that the value of the regularization parameter was so small, that the noise began to dominate the reconstructed images. For steps 114, 116, and 118, the regularization parameter was decreased to 0.001 while keeping the same stopping criterion as that in steps 104, 106, and 108.

The above specification and examples provide a complete description of the structure and use of illustrative embodiments. Although certain embodiments have been described above with a certain degree of particularity, or with reference to one or more individual embodiments, those skilled in the art could make numerous alterations to the disclosed embodiments without departing from the scope of this invention. As such, the various illustrative embodiments of the devices are not intended to be limited to the particular forms disclosed. Rather, they include all modifications and alternatives falling within the scope of the claims, and embodiments other than the one shown may include some or all of the features of the depicted embodiment. For example, components may be omitted or combined as a unitary structure, and/or connections may be substituted. Further, where appropriate, aspects of any of the examples described above may be combined with aspects of any of the other examples described to form further examples having comparable or different properties and addressing the same or different problems. Similarly, it will be understood that the benefits and advantages described above may relate to one embodiment or may relate to several embodiments.

The claims are not intended to include, and should not be interpreted to include, means-plus- or step-plus-function limitations, unless such a limitation is explicitly recited in a given claim using the phrase(s) "means for" or "step for," respectively.

What is claimed is:

1. An ultrasound transducer cap, comprising:
   a hollow body with an internal cavity that is adapted to receive an ultrasound transducer, the hollow body comprising:
      an ultrasound transducer window disposed along a length of the hollow body that is configured with parallel edges to provide an unblocked line of sight between the ultrasound transducer housed within the hollow body, and a rectal wall;
   a plurality of light emitters disposed along a first edge of the parallel edges and a second edge of the parallel edges of the ultrasound transducer window;
   a plurality of light detectors disposed along the first edge and the second edge of the ultrasound transducer window;
   wherein the plurality of light emitters on the first edge are oppositely disposed to the plurality of light detectors on the second edge and the plurality of light emitters on the second edge are oppositely disposed to the plurality of light detectors on the first edge such that each light emitter of the plurality of light emitters and each light detector of the plurality of light detectors form adjacent and alternating, colinear, matched pairs;
   wherein the plurality of light emitters and the plurality of light detectors are in a linear arrangement from a top portion of the ultrasound transducer window to a bottom portion of the ultrasound transducer window forming matched pairs of alternating light emitters and light detectors spaced apart by the ultrasound transducer window;
   an ultrasound fiducial located adjacent to at least one light emitter of the plurality of light emitters or at least one light detector of the plurality of light detectors; and
   a capacitive electrode disposed on an outer surface of the hollow body.

2. The ultrasound transducer cap of claim 1, wherein the capacitive electrode is a ring that surrounds one of the at least one light emitter of the plurality of light emitters and the at least one light detector of the plurality of light detectors.

3. The ultrasound transducer cap of claim 1, wherein the ultrasound transducer cap is clipped to the ultrasound transducer to secure the ultrasound transducer cap to the ultrasound transducer.

4. The ultrasound transducer cap of claim 1, wherein the capacitive electrode is a copper pad.

* * * * *